United States Patent

Rau

[11] Patent Number: 6,121,215
[45] Date of Patent: Sep. 19, 2000

[54] FOAMING EFFERVESCENT BATH PRODUCT

[75] Inventor: Allen H. Rau, Cincinnati, Ohio

[73] Assignee: PHYZZ, Inc., Cincinnati, Ohio

[21] Appl. No.: 09/384,431

[22] Filed: Aug. 27, 1999

[51] Int. Cl.[7] ............ C11D 17/02; C11D 3/10; C11D 3/60

[52] U.S. Cl. .......... 510/130; 510/135; 510/141; 510/145; 510/151; 510/156; 510/445; 510/474; 510/509; 510/511

[58] Field of Search ............. 510/130, 135, 510/151, 141, 145, 156, 445, 474, 509, 511; 424/466

[56] References Cited

U.S. PATENT DOCUMENTS

| | | | |
|---|---|---|---|
| 3,328,307 | 6/1967 | Schmitz | 510/104 |
| 3,607,759 | 9/1971 | Barth . | |
| 4,093,710 | 6/1978 | Sass et al. . | |
| 4,252,664 | 2/1981 | Inamorato . | |
| 4,574,053 | 3/1986 | Kinsman et al. | 510/141 |
| 4,613,497 | 9/1986 | Chavkin . | |
| 4,666,707 | 5/1987 | Eguchi et al. . | |
| 4,753,792 | 6/1988 | Aberg . | |
| 4,806,357 | 2/1989 | Khan et al. . | |
| 4,852,201 | 8/1989 | Wundrock et al. . | |
| 4,879,105 | 11/1989 | Yorozu | 424/44 |
| 4,919,918 | 4/1990 | Cole et al. . | |
| 4,929,378 | 5/1990 | Morita et al. | 510/130 |
| 4,971,785 | 11/1990 | Wilson et al. . | |
| 5,002,758 | 3/1991 | Ichii et al. . | |
| 5,015,408 | 5/1991 | Reuss . | |
| 5,110,603 | 5/1992 | Rau | 424/466 |
| 5,141,666 | 8/1992 | Yorozu et al. | 510/102 |
| 5,198,144 | 3/1993 | Ichii et al. | 510/101 |
| 5,306,439 | 4/1994 | Lockhart . | |
| 5,431,841 | 7/1995 | Lockhart . | |
| 5,529,788 | 6/1996 | De Senna . | |
| 5,578,562 | 11/1996 | Lockhart . | |
| 5,593,693 | 1/1997 | Gergely et al. . | |
| 5,624,465 | 4/1997 | Harris . | |
| 5,683,976 | 11/1997 | Colurciello, Jr. et al. . | |
| 5,736,158 | 4/1998 | Quast . | |
| 5,736,494 | 4/1998 | Colurciello et al. . | |
| 5,783,537 | 7/1998 | Ahmed et al. . | |
| 5,804,546 | 9/1998 | Hall . | |
| 5,824,629 | 10/1998 | Petritsch | 510/120 |
| 5,955,057 | 9/1999 | Maunder et al. . | |

FOREIGN PATENT DOCUMENTS

| | | |
|---|---|---|
| 61-243014 | 10/1986 | Japan . |
| 02115116 | 4/1990 | Japan . |
| 04100900 | 4/1992 | Japan . |
| 06271455 | 9/1994 | Japan . |
| 08319228 | 12/1996 | Japan . |
| 09002942 | 1/1997 | Japan . |

*Primary Examiner*—Lorna M. Douyon
*Attorney, Agent, or Firm*—Piper Marbury Rudnick & Wolfe LLP; Steven B. Kelber

[57] ABSTRACT

A foaming effervescent bath composition is comprised of an effervescent base together with an anhydrous surfactant. The effervescent base may be sodium carbonate and an organic acid, or similar variations. The base is selected so as to provide a composition which has a high dissolution rate, of at least 0.4 g/sec. The product is designed so as to have a low density, not greater than about 1.0 g/cc. Surfactants that exhibit a high viscosity in the presence of low concentrations of salt give particularly good foaming performance. Other agents, such as a colorant, fragrance, humectant, or emollient, may be added.

13 Claims, No Drawings

FOAMING EFFERVESCENT BATH PRODUCT

BACKGROUND OF THE INVENTION

Field of the Invention

This invention pertains to effervescent compositions that deliver substantial amounts of foam for a satisfactory bath product. A low density product, employing specific surfactants, provides substantial amounts of foam to provide an aesthetically acceptable bathing product.

BACKGROUND OF THE PRIOR ART

Many types of bath products are well known. Some bath products such as bath salts and bath tablets are designed simply to add fragrance and/or color to the bath water. Other bath products such as bath oils add emollients, humectants and/or skin conditioners to the bath water. Still other bath products are designed to create copious amounts of foam on the surface of the bath water. These foaming bath products are generally liquids (foam baths) or solids (bath powders, beads, or granules). Foaming bath products all contain suitable types and amounts of surfactants to create lather.

Effervescent compositions are also well known. These products combine carbonate salts such as sodium carbonate and/or sodium bicarbonate with acidic materials such as citric, malic, or fumaric acid in a way that carbon dioxide gas is generated by the neutralization reaction that occurs when the acid and carbonate come into intimate contact with each other. Naturally, situations that allow the materials to dissolve in close proximity to each other accelerate the reaction.

A generic chemical equation for the effervescent reaction is:

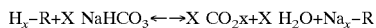

$$H_x\text{-}R + X\ NaHCO_3 \leftarrow \rightarrow X\ CO_2 + X\ H_2O + Na_x\text{-}R$$

where X indicates the valence of the particular acid (R) used, and Na can be replaced by any appropriate cationic ion.

Since the presence of water can initiate the effervescent reaction, these products must be formulated, manufactured, and packaged in ways that prevent unintended contact with moisture.

Several processes are commonly used to produce effervescent products. A common practice involves combining essentially anhydrous materials in a formula matrix that can be compressed directly using a conventional tablet press. An alternate to the direct compression process is to form flowable granules of the formulation using a solvent such as water or ethanol to bind the materials. The solvent is then removed from the granules in a drying process and the granule is then compressed into its final form on a tablet press. Products manufactured by either of these processes tend to be quite dense due to the high forces of compaction incurred in the tablet press.

A third process for making effervescent products involves using a very small amount of water to initiate a reaction between the organic acid and the carbonate or bicarbonate salt. This neutralization reaction creates additional water and the salt of the acid which, it is hypothesized, forms at the interface of the acid and carbonate material, preventing them from reacting further and thus stabilizing the resulting product. This process apparently "fuses" the acid and carbonate reactants into a shelf-stable form that can be molded into a desired shape and does not require sophisticated moisture-resistant packaging. Also, since the high compression forces inherent in tableting processes are not needed in this process, the finished items are less dense than those made by the first two methods. This process is a preferred method for manufacturing highly consumer-acceptable effervescent bath products that can be used to deliver fragrance and other oils to the bath water.

Surfactants have been combined with effervescent bases. For instance, effervescent denture cleanser tablets commonly use a small amount of surfactant to help achieve their cleaning performance. Surfactants that are commercially available in anhydrous or nearly anhydrous forms are obviously preferred for use in these formulations since any water that they bring with them would tend to initiate the effervescent reaction.

It would seem obvious that inclusion of a surfactant into an effervescent product would create a desirable foaming bath product. However, the creation of this product has apparently been elusive. Attempts to incorporate high foaming surfactants into these products have failed to yield an acceptable bathing product. We are unaware of any commercially available foaming effervescent bath products.

To help understand why it has been difficult to create high foaming effervescent products, it must be remembered that four things must be present and properly balanced to achieve copious foam. These items are water, surfactant, gas, and agitation. If they are not present in the proper proportions, foam either cannot be created at all or it is so weak as to not be consumer-acceptable.

In the case of foaming bath products, the bath provides the water; the surfactant is delivered from the product; the gas can be provided by a combination of ambient air and the carbon dioxide liberated in the effervescent reaction. Agitation is provided by the violence of the effervescent reaction and by the force of the water being added to the bathtub.

When the product is denser than water, as in the case of an effervescent tablet, it will sink to the bottom of the tub. In this situation, the only gas that is present is the carbon dioxide resulting from the effervescent reaction. This reaction is also the source of the only agitation that is present. Generally, even though there is ample water and surfactant present, there is not enough gas or agitation to create acceptable foam.

If the product can be made less dense than water, it will float, allowing the reaction to take place at the surface of the water. This permits the violent effervescent reaction to mix air in with the water, carbon dioxide and surfactant, thus creating copious foam. Thus the "molding" process discussed above would seem to be an ideal way to manufacture foaming effervescent bath products. However, attempts to add surfactants to these products have heretofore been unsuccessful.

U.S. Pat. No. 5,824,629 relates to hair cleansing tablets that release $CO_2$ and contain at least one surfactant. The covered compositions are small gas-generating tablets (0.5–2.5 cm$^3$) which contain 25–45% surfactant and 3–12% additives for hair and scalp care and 1–5% auxiliary compounds. These tablets are much too small to generate adequate foam for satisfactory bathing. Further, since they are apparently compressed using tablet-making technology, they will be too dense to foam well in a bathtub.

U.S. Pat. No. 5,804,546 teaches an effervescent cleaning composition in which the acid and carbonate components are aqueous solutions. These two components are physically isolated from each other by using multiple packages. The surfactants are combined with the carbonate solution. The effervescent reaction is initiated by combing the two solutions. Stable solid product forms are completely different from liquid forms of this type that physically isolate the reactive components.

U.S. Pat. No. 5,783,537 covers an enzymatic composition used for cleaning drains. It is a powder mixture that includes, among other materials, an effervescent base and a surfactant. No bathing composition is set forth.

U.S. Pat. No. 5,736,494 is a carpet cleaner. It contains surfactant and carbonate salts. 0–5% organic acid can be added optionally to adjust pH. Although acid and carbonate salt may be present, this product cannot be considered effervescent.

U.S. Pat. No. 5,736,158 discloses effervescent denture cleansers that incorporate, among other things, at least one surfactant from about 3% to about 18%. Sodium lauryl sulfate is shown as the surfactant in the examples. There is no discussion of foaming performance or of physical form requirements for the surfactant.

U.S. Pat. No. 5,683,976 teaches a powder carpet cleaning composition that contains surfactant, carbonate salts, and an acid. The acid is simply used to adjust the pH of the composition, not to provide effervescence.

U.S. Pat. No. 5,624,465 relates to an internally-carbonating cleansing composition. It requires separate liquid carbonate and acid solutions that are mixed at the point of use to generate carbon dioxide. As such, it does not represent a solid form effervescent product.

U.S. Pat. No. 5,593,693 teaches an invention in which a surfactant is incorporated in an effervescent material. The function of the surfactant in this case is to aid the suspension of a pharmaceutical active ingredient. At column 2, line 58, it is noted that foam formation is undesirable.

U.S. Pat. No. 5,578,562, U.S. Pat. No. 5,431,841, and U.S. Pat. No. 5,306,439 are related patents that teach cleaner formulations comprised of citric acid, sodium bicarbonate and detergent. These compositions are compressed to be dense so that their dissolution times are at least 15 minutes. Further these patents teach that the amount of surfactant used (18–34%) reduces the amount of foam formed by the effervescent reaction.

U.S. Pat. No. 5,529,788 discloses an enzyme-containing effervescent tablet in which a surfactant is also included. There is no mention of foam generation as that is not an important performance parameter of the product.

U.S. Pat. No. 5,015,408 teaches an effervescent denture cleanser tablet. Surfactants are included at relatively low levels and the product is a dense tablet form. It is unlikely this type of formulation would generate enough foam for a satisfactory bath.

U.S. Pat. No. 4,971,785 and U.S. Pat. No. 4,919,918 address non-alcoholic ingestible delivery systems. These products are dry (tablet or granule) dosage forms that include a spray-dried essential oil, a surfactant and, optionally in the case of 4,971,785, an effervescent system. While the surfactant can cause foam formation, its primary function is to disperse the active, rendering the use of alcohol unnecessary. The ability to generate a large amount of foam is not discussed.

U.S. Pat. No. 4,852,201 is a toilet bowl cleaner. The invention is a tool that holds a cleaning pad. The composition of a tablet or powder effervescent cleaning composition for use in the pad is described. There is no reason to suspect that this composition would be suitable for a foaming bath product.

U.S. Pat. No. 4,806,358 encompasses an effervescent ibuprofen composition. A small amount of surfactant is included, presumably as a processing aid. There is no discussion of foaming performance.

U.S. Pat. No. 4,753,792 is similar to U.S. Pat. Nos. 4,806,358, 4,971,785 and 4,919,918. It is another effervescent oral tablet that contains a surfactant as a wetting agent. High volume foam generation is not discussed.

U.S. Pat. No. 4,613,497 discloses dry, water-foamable pharmaceutical compositions. These compositions are built on effervescent bases. The foam is formed by combining the effervescent couple with a water soluble polysaccharide gum and a gelling salt. No surfactants are used. There is no reason to expect that this type of foam would be sufficient for a bath product.

U.S. Pat. No. 4,252,664 covers a laundry detergent composition that includes effervescent granules. Fatty acid is used in the production of the effervescent granule. High foaming performance is not suggested by this composition.

U.S. Pat. No. 5,002,758 claims a fumaric acid based effervescent composition comprising a carbonate, carboxymethyl cellulose or polyethylene glycol, and a nonionic surfactant. The nonionic surfactant is present to wet the fumaric acid, preventing it from floating. Foam generation is not anticipated.

U.S. Pat. No. 4,666,707 discusses effervescent compositions that are weakly acidic and contain moisturizers. The moisturizers taught in this patent appear to be humectants.

U.S. Pat. No. 4,093,710 is directed to granules of potassium chloride, prepared by granulating an alkali metal carbonate together with an anhydrous granular organic acid such as citric acid, together with a polyethylene glycol. The resulting granules are free flowing, and effervesce, providing a carrier for pharmaceutical agents or nutrients. No foam preparation or generation is described.

U.S. Pat. No. 3,607,759 describes surfactant-containing effervescent denture soak tablets. This product is produced using 3–5 tons of pressure. The result will be a dense product that will not be capable of producing the copious foam needed for a bath product.

SUMMARY OF THE INVENTION

An aesthetically pleasing, foaming bath product is prepared from an effervescent base, one or more surfactants capable of producing a high level of foam, with the product being formulated to give an overall positive buoyancy, that is, a low density product. The effervescent base, typified by a carbonate or bicarbonate and an organic acid, preferably provide rapid effervescence, to enhance mechanical agitation. Since mechanical agitation occurs, due to the low density, at the surface of the water, rather than that at the bottom of the tub, the effervescence itself is sufficient to ensure foaming that is aesthetically acceptable.

The surfactant may be specifically selected on the basis of viscosity in the presence of electrolytes. Surfactants that provide a viscosity in excess of 500 cps at a concentration of NaCl of 0.66% (w/w) and are otherwise acceptable for contact with human skin constitute one embodiment within this class.

DETAILED DESCRIPTION OF THE INVENTION

The aim of this invention is to provide an effervescent bath product that delivers an acceptable amount of foam. To provide the unique foaming characteristics of this invention, at least four elements or goals must be met. The surfactant selected must be anhydrous or nearly anhydrous. The product, which includes an effervescent base and the surfactant, must have a density substantially equal to, or less than, 1 gram/cc, so that the resulting product floats on the bath water surface, or only slightly below. The product needs to have a rapid dissolution time, that is, the effervescent base must react rapidly. The surfactant should be capable of producing a consumer acceptable foam. In one embodiment, the surfactant or surfactants selected preferably have a relatively high viscosity in salt solutions, above about 500 cps at a NaCl concentration of 0.66%, where the surfactant is present in an amount of 10% (w/w).

The critical components of the invention are: an effervescent base, one or more surfactants capable of producing a high level of foam, and a full-product composition that has a density equal to or less than about 1 gram/cc. Cosmetic additives such as (but not limited to) color, fragrance, emollients and humectants can be added at the formulator's option.

Representative humectants include polyethylene, glycol, glycerin, polyvinyl alcohol, sorbitol and polyvinylpyrollidone. Emollients may include mineral oils, fatty acid esters, fatty alcohols, dimethicones, etc.

The effervescent portion is designed by combining an alkaline carbonate salt (or salts) such as sodium carbonate or sodium bicarbonate with an acid, diacid or triacid such as citric acid, malic acid, fumaric acid, succinic acid or tartaric acid. More than one acid and/or more than one carbonate salt may be used, if desired. The exact combination of acidic and alkaline materials can be varied in order to give an acidic or alkaline pH. They can also be varied to effect the stability and physical properties of the finished product.

Broadly, the carbonate or bi-carbonate salts must be selected, together with the organic acid, to provide a rapidly evolving effervescent base. A dissolution rate of at least 0.4 grams per second, preferably at least 0.5 grams per second, is a target rate. Although preferred acids, diacids and triacids are described above, alternative acids including acetic acid, propionic and butyric acid and valeric acid may be used. Among diacids, oxalic, glutaric, adipic and malonic acid may be used. These may be combined with the carbonate salts described above, or others known to those of skill in the art, including sodium sesquicarbonate, potassium hydrogen carbonate, potassium carbonate, ammonium hydrogen carbonate, ammonium carbonate and ammonium sesquicarbonate.

The surfactant is generally anionic, although the use of nonionic, amphoteric and cationic surfactants can be employed. Surfactant blends that generate sufficient foam are also conceivable. Sodium Methyl Oleoyl Taurate and Sodium Lauryl Sulfoacetate are preferred surfactants.

The acid component of the inventive composition is generally present in amounts of 2–50%, by weight, of the product. Surfactant(s) will be included in amounts of 1–15% by weight of the total product, while the carbonate or bicarbonate component may be included in amounts of 35–95% by weight of the composition. Fragrance, colorants, humectants and emollients, collectively, may be present in amounts of 0–10% by weight.

It is important to note that while the product is essentially anhydrous, individual components, e.g., acid and surfactant, as well as optional additives, may be liquid or solid. "Essentially anhydrous" as used herein, indicates the component or product comprises no more than about 1% (by weight) water.

It is important that the product density be equal to or less than about 1 gram/cc. This assures that the product will float on the bath water surface during use. Floating assures that air is incorporated into the foam while the product is effervescing. If the product density is significantly greater than 1 gram/cc the product will sink to the bottom of the tub. This prevents ambient air from being incorporated in the foam and thus yields an unsatisfactory, weak foam layer. The required product density can be achieved by process and/or by formulation. Specifically, using the "molding process" described above, the mass of product to be formed can be adjusted to the desired volume of the item such that the density requirement is met. Since the high-pressure compaction inherent in tablet-making processes is avoided, low-density products are possible. Alternatively, lightweight materials such as certain grades of maltodextrin, starch and/or silica can be incorporated in the product to help assure the proper density.

The speed of effervescence is also important to the performance of the product. The faster the product effervesces, the more mechanical agitation occurs. This action helps "whip up" the foam on the water surface. It appears that a dissolution rate of at least approximately 0.4 grams per second, preferably at least 0.5 grams per second, is needed to achieve good foam.

The following data illustrates the invention. The base formula used is:

| Material | % (w/w) |
|---|---|
| Citric Acid | 25.0 |
| Sodium Bicarbonate | 70.0 |
| Surfactant (see below) | 4.0 |
| Fragrance | 1.0 |

| Surfactant | Diameter (inches) | Weight (grams) | Density (gm/cm$^3$) | Dissolution Time (sec) | Dissolution Rate (grams/sec) | Foam Acceptability |
|---|---|---|---|---|---|---|
| Sodium Methyl Oleoyl Taurate | 2½ | 120.6 | 0.90 | 115 | 1.05 | Excellent |
| Sodium Methyl Oleoyl Taurate | 3 | 215.5 | 0.93 | 105 | 2.05 | Excellent |
| Sodium Lauryl Sulfoacetate | 2½ | 117.4 | 0.88 | 370 | 0.32 | Fair |
| Sodium Lauryl Sulfoacetate | 3 | 217.5 | 0.94 | 450 | 0.48 | Good |
| Sodium Lauryl Sulfate | 2½ | 101.0 | 0.75 | 670 | 0.15 | Poor |
| Sodium Lauryl | 3 | 214.3 | 0.93 | 855 | 0.25 | Poor |

-continued

| Surfactant | Diameter (inches) | Weight (grams) | Density (gm/cm$^3$) | Dissolution Time (sec) | Dissolution Rate (grams/sec) | Foam Acceptability |
|---|---|---|---|---|---|---|
| Sulfate | | | | | | |
| Sodium C14–16 Olefin Sulfonate | 2½ | 110.4 | 0.82 | >900 | <0.12 | Poor |
| Sodium C14–16 Olefin Sulfonate | 3 | 191.8 | 0.83 | >900 | <0.21 | Poor |
| Disodium Lauryl Sulfosuccinate | 2½ | 116.3 | 0.87 | 840 | 0.14 | Poor |
| Disodium Lauryl Sulfosuccinate | 3 | 199.8 | 0.86 | >900 | <0.22 | Poor |
| Sodium Cocoyl Isethionate | 2½ | 110.2 | 0.82 | 525 | 0.21 | Poor |
| Sodium Cocoyl Isethionate | 3 | 224.7 | 0.97 | 740 | 0.30 | Poor |

These balls were made using the molding process discussed above by following this procedure:

Citric acid, sodium bicarbonate and fragrance were combined in a planetary mixer and mixed for 2 minutes. With the mixer running, this powder mix was sprayed with approximately 0.6–0.7% (based on the total batch weight) distilled water. This blend was mixed for approximately 45 seconds. The surfactant was added and mixed for approximately 30 seconds. Aliquots of the final mixture were placed into 2½ inch and 3 inch spherical molds and allowed to sit overnight. The balls were de-molded and allowed to equilibrate for 5 days prior to evaluation.

Evaluations were conducted by the following methods:

Weight was determined by weighing on a standard laboratory balance. Density was calculated by dividing the weight in grams by 134.07 (volume in cm$^3$) for the 2½" sphere or 231.67 for the 3" sphere.

Dissolution time was determined by placing approximately 20 liters of 40° C. tap water in a standard stainless steel kitchen sink (21"×15¼", filled to a depth of approximately 4"). The time for the product to completely dissolve was noted. Subjective evaluations of the foam quantity and quality were made. After the product completely dissolved, approximately 4 liters of 40° C. tap water was added to the sink at a rate of about 6 liters per minute. The effect of this added agitation on the foam was noted. The overall subjective acceptability of the foam was recorded.

For comparison purposes, prototypes were made using a high pressure tableting process. The same formula as above was used. Tablets (~100 gram) were compressed using a Carver press and a 2¼" circular die. Approximately 7000 pounds of pressure were applied. Density was calculated using the volume of a 2¼" cylinder with the measured thickness.

Dissolution time and foam quality tests were run as above. Data are:

| Surfactant | Thickness (inches) | Weight (grams) | Density (gm/cm$^3$) | Dissolution Time (sec) | Dissolution Rate (grams/sec) | Foam Acceptability |
|---|---|---|---|---|---|---|
| Sodium Methyl Oleoyl Taurate | 1¹⁄₁₆ | 98.9 | 1.43 | 265 | 0.37 | Fair |
| Sodium Lauryl Sulfoacetate | 1¹⁄₁₆ | 99.1 | 1.43 | 365 | 0.27 | Fair |
| Sodium Lauryl Sulfate | 1¹⁄₁₆ | 99.5 | 1.44 | 620 | 0.16 | Poor |
| Sodium C14–16 Olefin Sulfonate | 1¹⁄₁₆ | 99.5 | 1.44 | >900 | <0.11 | Poor |
| Disodium Lauryl Sulfosuccinate | 1¹⁄₁₆ | 99.5 | 1.44 | 525 | 0.19 | Poor |
| Sodium Cocoyl Isethionate | 1¹⁄₁₆ | 99.3 | 1.43 | 345 | 0.29 | Fair |

These data clearly show that lower density products, particularly those formulated with Sodium Methyl Oleoyl Taurate or Sodium Lauryl Sulfoacetate, are superior to their high-density tableted counterparts.

The superior performance of Sodium Methyl Oleoyl Taurate and Sodium Lauryl Sulfoacetates surfactant may be due to the fact that they form fairly high viscosity fluids in the presence of a relatively small amount electrolyte. The other tested surfactants do not exhibit this property. Data supporting this theory are:

| | Viscosity (cps) at 40° C. in the presence of indicated NaCl level | | | | | |
|---|---|---|---|---|---|---|
| Surfactant (10% w/w) | 0% | 0.66% | 1.64% | 3.23% | 4.76% | 6.25% |
| Sodium Methyl Oleoyl Taurate | 35 | 1588 | 82,000 | >100,000 | 6400 | 40 |
| Sodium Lauryl Sulfoacetate | 1675 | 6400 | 900 | 15 | — | — |

-continued

| | Viscosity (cps) at 40° C. in the presence of indicated NaCl level | | | | | |
|---|---|---|---|---|---|---|
| Sodium Lauryl Sulfate | 5 | 10 | 10 | 410 | 7400 | 17,200 |
| Sodium C14–16 Olefin Sulfonate | 5 | 5 | 10 | 7.5 | 7.5 | 25 |
| Disodium Lauryl Sulfosuccinate | 5 | 5 | 5 | 5 | — | — |
| Sodium Cocoyl Isethionate | 5 | 5 | 5 | 7.5 | 20 | — |

This performance is germane to this invention. Electrolytes, sodium chloride being the usual model, are well known and often used to modify the viscosity of many surfactants. Generally adding salt builds viscosity to a maximum point. Beyond this concentration, additional salt will decrease the surfactant's solution viscosity. The components of effervescent systems (organic acids, carbonate salts, and their reaction products) ionize readily and thus can be expected to act as electrolytes when placed in solution. As such, their effect on surfactant behavior may be important to product performance.

The fact that the preferred surfactants have markedly different viscosity versus salt concentration curves than the other surfactants may be important to the product's performance. The higher viscosity of the surfactant solution in this salt range helps create a more stable foam. On the other hand, one can also theorize that the surfactants that have lower viscosities in the presence of salt allow moisture to more easily penetrate the product, thus de-stabilizing it. The lengthy dissolution times exhibited by these products may lend some credence to this theory.

In net, the following parameters seem to be essential to achieving an acceptable foaming effervescent bath product:
1. An effervescent couple (organic acid and carbonate salt)
2. Surfactant capable of producing a consumer acceptable foam
3. Low density to assure that the product will float
4. Rapid dissolution rate.

The invention of this application as described above both generically, and with regard to specific embodiments. A wide variety of alternatives known to those of skill in the art can be selected within the generic disclosure, and examples are not to be interpreted as limiting, unless specifically so indicated. As particular examples, fragrances, colorants, humectants and emollients are known to those of skill in the art in non-foaming or adequately foaming effervescent products, and the same may be employed herein with equal facility. The invention is not otherwise limited, except for the recitation of the claims set forth below.

What is claimed is:

1. A non-tableted solid foaming bath composition, comprised of:

an effervescent base comprised of a salt of a carbonate or bi-carbonate and a solid organic acid, diacid or triacid, said composition further comprising an essentially anhydrous surfactant, which said composition has a density of no more than about 1.0 g/cc, said composition floats on water surface, and said composition exhibits a dissolution rate in water of at least about 0.4 g/sec, as measured at 40° C.

2. The composition of claim 1, wherein said surfactant, when present in an aqueous solution in an amount of 10% (w/w) exhibits a viscosity, in a NaCl concentration of 0.66%, of at least 500 cps.

3. The composition of claim 1, wherein said composition further comprises at least one of a fragrance, a colorant, a humectant and an emollient.

4. The composition of claim 2, wherein said composition further comprises at least one of a fragrance, a colorant, a humectant and an emollient.

5. The composition of claim 1, wherein said rate of dissolution is at least about 0.5 g/sec.

6. The composition of claim 1, wherein said composition is in the form of a, wafer or molded shape.

7. The composition of claim 1, wherein said composition comprises low density filler so as to achieve said density of no more than about 1.0 g/cc.

8. The composition of claim 7, wherein said low density filler comprises low density maltodextrin, starch or silica.

9. The composition of claim 1, wherein said surfactant comprises sodium methyl poleoyl taurate or sodium lauryl sulfoacetate.

10. A method of making the non-tableted solid foaming bath composition of claim 1, comprising mixing said salt, organic acid and anhydrous surfactant together, combining said mixed product with a minor amount of water and thoroughly mixing to obtain a final mixture, placing said mixture into a mold, and removing said mixture from said mold after stabilization.

11. The method of claim 10, wherein said period of stabilization is at least two hours.

12. The method of claim 10, wherein said water is present in no more than 1.0%, based on total weight.

13. A method of producing a foam, comprising combining the bath composition of claim 1 with a volume of water.

* * * * *

UNITED STATES PATENT AND TRADEMARK OFFICE
CERTIFICATE OF CORRECTION

PATENT NO. : 6,121,215  
DATED : September 19, 2000  
INVENTOR(S) : Allen H. Rau Page 1 of 1

It is certified that error appears in the above-identified patent and that said Letters Patent is hereby corrected as shown below:

<u>Column 10,</u>  
Line 36, please delete "poleoyl" and insert therefor -- oleoyl --.

Signed and Sealed this

Eighth Day of January, 2002

Attest:

JAMES E. ROGAN  
Attesting Officer     Director of the United States Patent and Trademark Office